(12) United States Patent
Headley et al.

(10) Patent No.: US 9,073,304 B2
(45) Date of Patent: Jul. 7, 2015

(54) CONVEYING APPARATUS WITH AN AIR-SEPARATED BACKING MATERIAL

(75) Inventors: Steven C. Headley, Arlington, TX (US); Alan M. Then, Plano, TX (US); Rui Xu, Plano, TX (US); Mark Rasmussen, Sulphur Springs, TX (US)

(73) Assignee: Advanced Vision Technology (A.V.T.) Ltd., Hod Hasharon (IL)

( * ) Notice: Subject to any disclaimer, the term of this patent is extended or adjusted under 35 U.S.C. 154(b) by 543 days.

(21) Appl. No.: 13/323,215

(22) Filed: Dec. 12, 2011

(65) Prior Publication Data

US 2013/0003063 A1 Jan. 3, 2013

Related U.S. Application Data

(60) Provisional application No. 61/421,738, filed on Dec. 10, 2010, provisional application No. 61/567,933, filed on Dec. 7, 2011.

(51) Int. Cl.
*G01J 3/46* (2006.01)
*G01B 11/28* (2006.01)
(Continued)

(52) U.S. Cl.
CPC .............. *B41F 33/0036* (2013.01); *B65H 3/14* (2013.01); *B65H 18/28* (2013.01);
(Continued)

(58) Field of Classification Search
CPC ............ B41F 33/0036; B41P 2233/51; B41P 2233/00; B41P 2233/50; G01N 2021/8917; G01N 2021/8455; G01N 2021/258–2021/399; G01N 2021/845; G01J 3/46–3/528; D21H 5/007; D21H 25/16; B65H 3/14; B65H 5/22; B65H 5/228; B65H 7/16; B65H 18/26; B65H 20/10; B65H 29/24; B65H 29/245–29/248; B65H 51/26; B65H 2301/41414; B65H 2301/41425; B65H 2301/41446; B65H 2301/4461; B65H 2301/51533

USPC .......... 356/429–431, 402–425, 237.1–237.5, 356/444, 72, 73, 239.1–239.8; 198/377.03, 198/377.08, 428, 438, 373
See application file for complete search history.

(56) References Cited

U.S. PATENT DOCUMENTS 4,319,847 A * 3/1982 Howarth ........................ 356/431
4,683,380 A * 7/1987 Shipkowski et al. .......... 250/548
(Continued)

FOREIGN PATENT DOCUMENTS

WO 2007-130280 A2 11/2007

OTHER PUBLICATIONS

Katsumi Aoki and Hiromu Hashimoto, Characteristics of Air Film Thickness and Flow Visualization for Transporting Film, Journal of Fluid Science and Technolog, 2010, 5(3), 503-514.*
(Continued)

*Primary Examiner* — Michael A Lyons
*Assistant Examiner* — Violeta A Prieto
(74) *Attorney, Agent, or Firm* — Brown Rudnick LLP

(57) ABSTRACT

A conveying apparatus for conveying an object, the object having at least a non-opaque portion, including a light source, an optical detector and a backing measurement apparatus, the light source for illuminating the object, the optical detector for acquiring information at least relating to at least one chromatic characteristic of the non-opaque portion, the backing measurement apparatus including a backing material, a backing support and a plurality of rollers, the backing material exhibiting at least one of determined chromatic characteristics and determined optical characteristics, the backing support for supporting the backing material, the plurality of rollers for rolling the backing material over the backing support, wherein light emitted by the light source optically interacts with the backing material consistently through the non-opaque portion.

37 Claims, 4 Drawing Sheets

(51) Int. Cl.

| | | |
|---|---|---|
| | *B65G 47/24* | (2006.01) |
| | *B41F 33/00* | (2006.01) |
| | *B65H 18/28* | (2006.01) |
| | *G01N 21/25* | (2006.01) |
| | *G01N 21/88* | (2006.01) |
| | *B65H 3/14* | (2006.01) |
| | *G01N 21/84* | (2006.01) |
| | *G01N 21/89* | (2006.01) |

(52) U.S. Cl.
CPC ............ *B41P 2233/51* (2013.01); *G01N 21/25* (2013.01); *G01N 2021/845* (2013.01); *G01N 2021/8917* (2013.01); *G01N 21/8806* (2013.01)

(56) References Cited

U.S. PATENT DOCUMENTS

| | | | |
|---|---|---|---|
| 4,715,715 A * | 12/1987 | Howarth et al. ............... 356/402 |
| 4,956,737 A | 9/1990 | Brock |
| 5,047,652 A | 9/1991 | Lisnyansky et al. |
| 5,056,431 A | 10/1991 | Sainio |
| 5,724,259 A | 3/1998 | Seymour et al. |
| 6,135,026 A | 10/2000 | Kalbantner et al. |
| 6,281,679 B1 | 8/2001 | King et al. |
| 6,382,100 B1 | 5/2002 | Satoh et al. |
| 7,627,141 B2 | 12/2009 | Noffke et al. |
| 7,892,399 B2 | 2/2011 | Graham et al. |
| 2003/0168614 A1 * | 9/2003 | Vogt et al. .................. 250/492.1 |
| 2004/0174574 A1 | 9/2004 | Okuda |
| 2007/0113748 A1 * | 5/2007 | Geissler et al. ............... 101/232 |
| 2008/0174771 A1 * | 7/2008 | Yan et al. .................... 356/237.5 |
| 2008/0193176 A1 * | 8/2008 | Roof .............................. 399/323 |
| 2009/0021807 A1 | 1/2009 | Horita |
| 2009/0059232 A1 * | 3/2009 | Hellstrom et al. ............ 356/429 |
| 2009/0141265 A1 * | 6/2009 | Shakespeare et al. .......... 356/73 |
| 2010/0003904 A1 * | 1/2010 | Duescher ...................... 451/259 |
| 2012/0105624 A1 * | 5/2012 | Lin et al. ...................... 348/125 |

OTHER PUBLICATIONS

ISO—"Graphic Technology—Spectral Measurement and Colorimetric Computation for Graphic Arts Images", Dated Jan. 23, 2009, 41 Pages.

"Short Communication. Automatic Inspection of the Pomegranate (*Punica granatum* L.) Arils Quality by Means of Computer Vision" J. Blasco et al., Spanish Journal of Agricultural Research 2008 6(1), 12-16.

"The Foundation of Color Measurement and Color Preception", by Wandell et al., Mar. 20, 1996, 30 Pages.

Hashimoto, 1999, Air Film Thickness Estimation in Web Handling Processes, Journal of Tribology 121(1):50-55.

\* cited by examiner

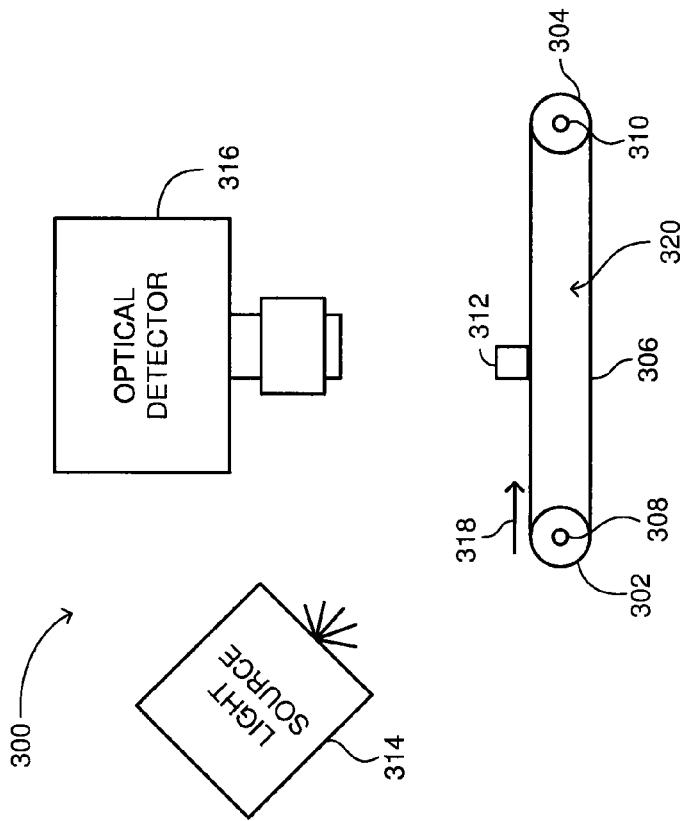
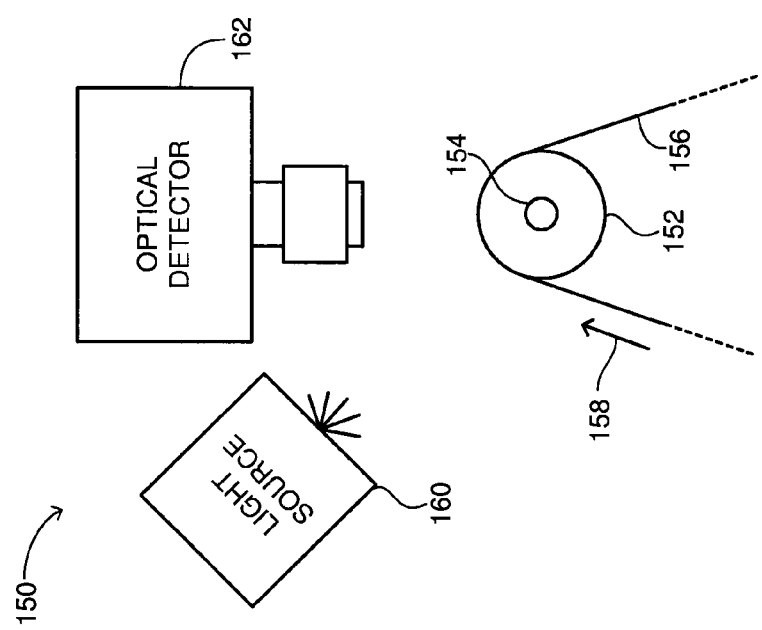
FIG. 3
FIG. 2

CONVEYING APPARATUS WITH AN AIR-SEPARATED BACKING MATERIAL

CROSS-REFERENCE TO RELATED APPLICATIONS

This claims priority to and the benefit of Provisional U.S. Patent Application Ser. No. 61/421,738 filed Dec. 10, 2010, and also Provisional U.S. Patent Application Ser. No. 61/567,933 filed Dec. 7, 2011. The entirety of each of these two provisional patent applications is hereby incorporated by reference herein.

FIELD OF THE DISCLOSED TECHNIQUE

The disclosed technique relates to conveying systems, in general, and to a printed material conveying apparatus suitable for color measurements, in particular.

BACKGROUND OF THE DISCLOSED TECHNIQUE

Spectral measurements of objects are required by various industries for different applications. The term 'object' herein refers to continuous printed substrates or discrete objects such as packages, fruits, vegetables, plastic toys, boxes and the like. For example, in the food industry, spectral measurements are used for sorting and quality control. In the biological materials industry, spectral measurements are used for the examination of dye markers absorbed by various cells or organisms, or to non-invasively identify pigments in a single cell or clusters of cells and to map the spatial organization of phototrophic groups in complex microbial communities. In the chemical industry, spectral measurements are used, for example, to identify the presence of pollutants in the air, by distinguishing the pollutants from the nitrogen, oxygen, water and other expected constituents.

In particular, spectral measurements are used in the printing industry for determining chromatic characteristics of objects. The chromatic characteristics may be represented, for example, by the estimated coordinates of a printed color in a color space (e.g., CIEXYZ, CIELUV, CIELAB, RGB, CYMK, HIS and the like), determined according to measurements of the light, which is either reflected from or transmitted through the object. The chromatic characteristics may further be represented by the optical reflection densities of the inks deposited on a printed substrate or an object. The chromatic characteristics may also be represented by the spectral composition of the light reflected from the printed substrate.

Objects, which at least a portion thereof, transmit at least a portion of incident light thereon, are herein referred to collectively as non-opaque objects. The term 'non-opaque' is defined, for example, in accordance with the ISO 13655 standard, where "opaque" is defined as a material with opacity greater than 99. A material behind the non-opaque objects may affect the reflectance factor of light impinging on the non-opaque objects. Alternatively, the material behind the non-opaque objects may affect the transmittance factor of light illuminating the non-opaque objects. When spectral measurements are made, the material behind the non-opaque object is referred to herein as a 'backing.' The reflectance factor can be defined as the ratio of light reflected from the printed substrate to light reflected from a perfect reflecting diffuser, both illuminated with the same light from the same direction. Similarly, the transmittance factor can be defined as the ratio of light transmitted through the object to light transmitted through a perfect transmitting diffuser, both illuminated with the same light from the same direction. The reflectance or transmittance factors may in turn affect the estimation of chromatic characteristics of the non-opaque objects, which are determined according thereto. For example, the reflectance factor is used when determining the X, Y and Z tristimulus values (e.g., according to the CIE 1931 XYZ color space) according to spectral measurements of the reflected light from the non-opaque object. Thus, for example, the determined X, Y and Z tristimulus values of a green color printed on a non-opaque material with a shiny aluminum backing will be different than the determined X, Y and Z tristimulus values of the same green color printed on the same non-opaque material with a white material backing.

To achieve repeatability and reproducibility of measurements of chromatic characteristics from a non-opaque object, as well as to provide a basis for comparing measurements between different measurement systems, a standard backing may be placed behind the non-opaque object during spectral measurements. During such spectral measurements, the printed material may need to be in proximate contact with the backing. The term 'repeatability of measurement' relates herein to a measurement of a sample, which can be repeated (i.e., for that same sample), with the same measuring instrument, under substantially the same measurement conditions, with substantially the same results (i.e., within a determined tolerance). The 'reproducibility of measurement' relates herein to a measurement of a sample, performed by an observer, with a measurement instrument, under specified measurement conditions, which can be reproduced by another observer, with substantially the same measurement instrument, under substantially the same measurement conditions, with substantially the same results (i.e., within a determined tolerance). For example, according to the ISO 13655 standard, the backing may be black, referred to as a black backing, or white, referred to as a white backing. Specifically, Annex A of the ISO 13655 standard defines the requirements of the white and black backings. The ISO 13655 standard further recommends that the measurements of light reflected off the non-opaque object, placed on and in contact with the backing, should be corrected relative to the reflection measurements of the backing alone. Similarly, other standards and industry accepted specifications such as those provided by the American Society for Testing and Materials (ASTM), the American National Standards Institute (ANSI), the Deutsches Institut für Normung (DIN), Fogra, and the Flexographic Technical Association (FTA), have various existing and evolving standards and specifications for colorimetric measurements. Such standards and specifications are, for example, FIRST, SNAP, Specifications Web Offset Publications (SWOP), General Requirements for Applications in Commercial Offset Lithography (GRACOL) and the like.

Systems and methods for the measurement of chromatic characteristics of non-opaque objects are known in the art. Also known in the art are methods and systems for stabilizing webs and measuring the thickness of webs. The publication "Short Communication. Automatic Inspection of the Pomegranate (*Punica granatum* L.) Arils Quality by Means of Computer Vision" by Blasco et al., is directed to a system for ensuring the quality and homogeneity of the color of commercial batches of pomegranate arils. The arils are singulated and transported over a conveyor belt. Images of the arils are acquired using two cameras to distinguish between arils and raw material by estimating the color of the objects and classifying the arils by size and color. The arils are separated into categories by means of air ejectors. The color of the conveying belts is selected to maximize the contrast, in the acquired image, between the arils and the background.

U.S. Pat. No. 5,056,431 to Sainio, entitled "Bernoulli-effect web stabilizer" is directed to a system and method for stabilizing a moving web within a printing press having one or more printing units. The system includes an air driven stabilizer structure disposed proximate to the printing units. The system stabilizes a printed web as it leaves a final print cylinder using a Bernoulli-effect stabilizer which is positioned proximate to the point where the web leaves the final print cylinder. A scanner, mounted in the vicinity of the stabilizer, accurately detects a desired printed image within a narrowly circumscribed depth-of-field. An air bar may be disposed immediately downstream of a print cylinder to reduce variations in the arc length of blanket follow. The air bar may also be disposed proximate to the upper surface of the web, where the surface tends to adhere to the print cylinder. By controlling the air pressure discharged from the air bar, the amount of blanket wrap may be maintained within predetermined limits. In another embodiment, the air bar may be disposed proximate to the lower surface of the web, such that the air discharged from the bar acts in a direction to increase blanket follow. Thus blanket follow may be precisely controlled and variations in blanket follow minimized.

U.S. Pat. No. 7,627,141 to Noffke et al., entitled "System and method for measuring color on a printing press" is directed to an image processing apparatus and method for measuring spatial and spectral information from an image of a printed substrate. In one embodiment the apparatus processes spatial and spectral information from the same acquired image using first and second processors. In another embodiment, a first acquired image may be used to process the spatial information and a second acquired image may be used to process the spectral information. The first and second acquired images may be acquired at separate times during the travel of the printed substrate, both images being acquired at same point on the printed substrate. The color of the printed substrate can be monitored based on the processed spatial and spectral information.

U.S. Pat. No. 7,892,399 to Graham et al., entitled "Local tension generating air stabilization system for web products" is directed to an air stabilization system employing two parallel, opposite-facing Coanda nozzles. Each nozzle exhausts gas at opposite directions and subjects a moving flexible web to opposing forces effective to create local tension within the web. Each nozzle includes an elongated slot that is perpendicular to the path of the moving web. The nozzles serve as different points along the machine direction for controlling the height of the web. The operative surface with the nozzles can exhibit a flush surface. The nozzles can be formed on elevated structures on the operative surface. The operative surface can be covered with a transparent substrate to minimize shape distortions on the moving web and to prevent debris from collecting around a sensor. By modulating the velocities of gases exiting the nozzles, the shape of the web can be manipulated to present a planar contour. The air stabilization system can be incorporated into a caliper scanner.

U.S. Pat. No. 6,281,679 to King et al., entitled "Web thickness measurement system" is directed to a non-contacting thickness measurement apparatus which is capable of on-line web thickness measurements. The apparatus is comprised of a first and second distance determining means and an x-y position adjustment means. The first and second distance determining means calculate a distance value from each distance determining means to a web surface. The distance determining means are on opposite sides of the web, so each distance determining means measures the distance to a different side of the web. At the same time, the distance between the two distance determining means is measured to produce a z-sensor spacing value. The two distance values are thereafter subtracted from the z-sensor spacing value to get a web thickness value. The x-y position adjustment means is used to keep the measurement spot on the web for the two distance determining means at the same location on the web.

U.S. Pat. No. 6,382,100 to Satoh et al., entitled "Web guide roller, and printing press incorporating the same" is directed to a roller assembly for pneumatically guiding a web of paper after it has been printed upon without the risk of smearing. The roller assembly is positioned downstream of a printing station in a web-fed rotary printing press. The assembly includes a roller in the form of a hollow cylinder defining a plenum chamber and having formed on its surface a multiplicity of air outlet openings in communication with the plenum chamber. Air supplied under pressure to the chamber is thus expelled from the air outlet openings in order to avoid contact between the roller and the web traveling over the roller. A baffle encloses at least part of the circumferential part of the roller surface for confining air expelled from the other circumferential part of the roller surface and for redirecting the confined air into a pair of spaces spaced between the web and the roller.

U.S. Pat. No. 6,135,026 to Kalbantner et al., entitled "Sheet guiding device in a sheet-fed printing press" is directed to a sheet guiding device assemblable from at least a first sheet guiding element and a second sheet guiding element. The sheet guiding device is for guiding sheets of printing material in a sheet-fed printing press and includes a guide for guiding at least one of the sheet guiding elements as the sheet guiding elements are being mutually assembled. In one embodiment of the sheet guiding device, at least one of the sheet guiding elements is embodied as a sheet guiding baffle provided with nozzles with the sheet guiding device including a radial fan for supplying the nozzles with blown air.

SUMMARY OF THE PRESENT DISCLOSED TECHNIQUE

It is an object of the disclosed technique to provide a novel method and system for consistently determining chromatic characteristics of objects which include non-opaque portions. In accordance with the disclosed technique, there is thus provided a conveying apparatus for conveying an object, the object having at least a non-opaque portion, the conveying apparatus including a light source, an optical detector and a backing measurement apparatus. The light source is for illuminating the object and the optical detector is for acquiring information at least relating to at least one chromatic characteristic of the non-opaque portion. The backing measurement apparatus includes a backing material, a backing support and a plurality of rollers. The backing material exhibits at least one of determined chromatic characteristics and determined optical characteristics, the backing support is for supporting the backing material and the plurality of rollers is for rolling the backing material over the backing support. The light emitted by the light source optically interacts with the backing material consistently through the non-opaque portion.

In accordance with another aspect of the disclosed technique, there is thus provided a conveying apparatus for conveying an object, the object having at least a non-opaque portion. The object is illuminated by a light source and an optical detector acquires information at least relating to chromatic characteristics of the non-opaque portion. The conveying apparatus includes at least a backing surface, the backing surface exhibiting at least one of determined chromatic characteristics and determined optical characteristics. The light emitted by the light source optically interacts with the backing surface consistently through the non-opaque portion.

BRIEF DESCRIPTION OF THE DRAWINGS

The disclosed technique will be understood and appreciated more fully from the following detailed description taken in conjunction with the drawings in which:

FIG. 2 is a schematic illustration of another printed material conveying apparatus, constructed and operative in accordance with another embodiment of the disclosed technique;

FIG. 3 is a schematic illustration of a further printed material conveying apparatus, constructed and operative in accordance with a further embodiment of the disclosed technique;

DETAILED DESCRIPTION OF THE EMBODIMENTS

The disclosed technique overcomes the disadvantages of the prior art by providing a conveying apparatus which includes a backing surface upon which objects which include non-opaque portions, are transported over in a production line. The term 'production line' refers herein to a line of machines which transform the state (e.g., color, shape, ascription and the like) of an object. Such machines are, for example, printing machines, coloring machines, sorting machines, impression machines and the like. The machines are connected by a conveying apparatus, which transports the objects along the production line.

The backing surface exhibits specific known chromatic characteristics such as spectral reflectance, lightness, chroma, hue, XYZ tristimulus values and other any chromatic characteristics which can be determined from the spectral reflectance, or optical characteristics, such as refractivity, diffusivity, fluorescence, and opacity, which conform to a given standard, or are intended for specific measurement conditions. The chromatic characteristics and optical characteristics of the backing surface should be determined with respect to the spatial distribution over the surface (i.e., how the characteristics change over the surface) and with respect to the temporal distribution (i.e., how the characteristics change over time). The backing surface may be a plate made of, or coated with a material exhibiting the aforementioned specific optical or chromatic characteristics. The backing surface may also be a roller or a cylinder made of, or coated with a material exhibiting the aforementioned specific surface characteristics. The backing surface may further be a belt coated with, or made of, a material, exhibiting specified surface characteristics. The belt rotates around two rollers as further explained below. The aforementioned specific surface characteristics may be specified by an international standard such as the ISO 13655 standard, or be designed to meet the needs of a specific combination of object characteristics and required measurement conditions. These measurement conditions may be lighting characteristics (e.g., intensity, spectral composition and the like), optical detector position and the like. For example, ink film thickness is measured using optical reflection densities (i.e., the logarithm to base ten of the ratio between the intensity of the light incident on the printed ink film and the intensity of the light reflected from the ink film). When measuring ink film thickness on a double-sided printed substrate, the substrate is placed on a black backing. Thus, inked areas on the non-inspected side do not significantly influence the measurements of the ink film thickness on the inspected side of the substrate.

Figure 1:
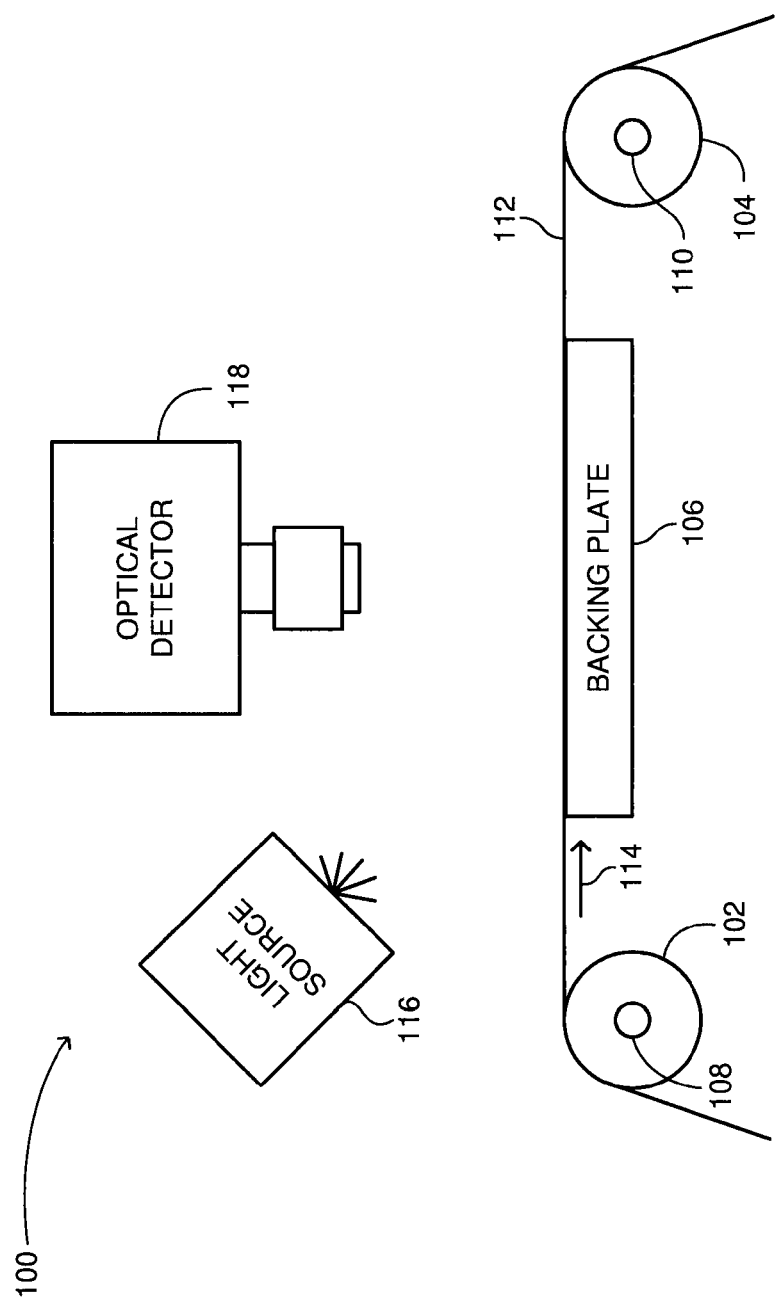
FIG. 1 is a schematic illustration of a printed material conveying apparatus, constructed and operative in accordance with an embodiment of the disclosed technique.

Reference is now made to FIG. 1, which is a schematic illustration of a printed material conveying apparatus (herein in referred to as simply a conveying apparatus), generally referenced 100, constructed and operative in accordance with an embodiment of the disclosed technique. Conveying apparatus 100 includes two rollers 102 and 104 and a backing plate 106. Each one of rollers 102 and 104 is rotatable about a respective axis 108 and 110. Each one of rollers 102 and 104 is coupled with a mechanical support (not shown) enabling its rotation thereof. Backing plate 106 is also coupled with a mechanical support (not shown). The mechanical supports, which support backing plate 106, roller 102 and roller 104, may be the same mechanical support or different mechanical supports. Backing plate 106 is made of, or is coated with, a material exhibiting specific determined chromatic characteristics (e.g., spectral reflectance, lightness, chroma and hue) and optical characteristics (e.g., refractivity, diffusivity, fluorescence and opacity). For example, backing plate 106 may be made of, or coated with, a white material, which complies with the backing characteristics specified in Annex A of the ISO 13655 standard.

Conveying apparatus 100 conveys a non-opaque object 112 such as a non-opaque printed substrate, for example, from a printing press to a cutting machine. Printed substrate 112 is made of, for example, paper, a flexible polymer, plastic, metal or a laminate of at least two materials. Printed substrate 112 moves in the direction indicated by an arrow 114 over roller 102, backing plate 106 and roller 104. As printed substrate 112 is rolled over backing plate 106, printed substrate 112 comes in proximate contact with backing plate 106. A light source 116 illuminates printed substrate 112 and backing plate 106 with a standard light (e.g., the CIE D65 illuminant, the CIE D50 illuminant, the CIE A illuminant and the like). The light emitted by light source 116 is either reflected from (i.e., either specularly or diffusively) or transmitted through backing plate 106. In other words, the light emitted by light source 116 optically interacts with backing plate 106. An optical detector 118, placed substantially over printed substrate 112, acquires information at least relating to the chromatic characteristics of printed substrate 112. In case the material from which backing plate 106 is made of is a light transmissive material, light source 116 may be located such that printed substrate 112 and backing plate 106 are positioned between optical detector 118 and light source 116. Optical detector 118 may be, for example, a spectrophotometer, a hyperspectral imager, a color camera (e.g., a line or area color camera employing a standard color space such as the CIE XYZ or RGB), a densitometer or a colorimeter. Thus when using backing plate 106, chromatic characteristics of printed substrate 112 acquired by different optical detectors will only differ due to the differences in the optical detectors and light sources used.

As mentioned above, the standard backing may be a roller coated with, or made of, a material exhibiting specified surface characteristics. Reference is now made to FIG. 2, which is a schematic illustration of another printed material conveying apparatus (herein in referred to as simply a conveying apparatus), generally referenced 150, constructed and operative in accordance with another embodiment of the disclosed technique. Conveying apparatus 150 includes a backing roller 152. Backing roller 152 is rotatable about a rod 154. Backing roller 152 is coupled with a mechanical support (not shown) enabling its rotation thereof. Backing roller 152 is coated with, or made of, a material exhibiting specific determined chromatic or optical characteristics. Similar to backing plate 106 (FIG. 1), backing roller 152 is made of, or is coated with, for example, a white material which complies with the backing material characteristics specified in Annex A of the ISO 13655 standard.

Conveying apparatus 150 conveys a non-opaque object 156 such as a printed substrate, for example, from a printing press to a cutting machine. Printed substrate 156 is a non-opaque material as defined above. Printed substrate 156 is made of, for example, paper, a flexible polymer, plastic, metal or a laminate of at least two materials. Printed substrate 156 moves in the direction indicated by arrow 158 over backing roller 152. As printed substrate 156 is rolled over backing roller 156, printed substrate 156 comes substantially into contact with backing roller 156. A light source 160 illuminates printed substrate 156 with a standard light. The light emitted by light source 160 is either reflected from or transmitted through backing roller 156. In other words, the light emitted by light source 160 optically interacts with backing roller 156. An optical detector 162, placed substantially over printed substrate 156, acquires information at least relating to the chromatic characteristics of printed substrate 156. In case the material from which backing roller 152 is made from is a light transmissive material, light source 160 may be located within backing roller 152. Thus, when using backing roller 152, the chromatic characteristics of a printed substrate acquired by different optical detectors will only differ due to the differences between the optical detectors and light sources used.

As mentioned above, the standard backing surface may be a belt coated with, or made of, a material exhibiting specified surface characteristics. This belt rotates about two rollers. Reference is now made to FIG. 3, which is a schematic illustration of a printed material conveying apparatus (herein in referred to as simply a conveying apparatus), generally referenced 300, constructed and operative in accordance with a further embodiment of the disclosed technique. Conveying apparatus 300 includes two rollers 302 and 304 and a backing belt 306. Each one of rollers 302 and 304 is rotatable about a respective axis 308 and 310. Each one of rollers 302 and 304 is coupled with a mechanical support (not shown) enabling the rotation thereof. Backing belt 306 is made of, or is coated with, a material exhibiting specific determined chromatic or optical characteristics.

Conveying apparatus 300 conveys a non-opaque object 312 (e.g., a package), which moves in the direction indicated by an arrow 318. As object 312 is conveyed over backing belt 306 a light source 314 illuminates object 312 and backing belt 306 with a standard light. The light emitted by light source 314 is either reflected from or transmitted through backing belt 306. In other words, the light emitted by light source 314 optically interacts with backing belt 306. In case the material from which backing belt 306 is made from is a light transmissive material, light source 314 may be located such that backing belt 306 is positioned between optical detector 316 and light source 314 (e.g., in gap 320). An optical detector 316, placed substantially over backing belt 306, acquires information at least relating to the chromatic characteristics of object 312. Thus when using backing belt 306 chromatic characteristics of object 312, acquired by different optical detectors, will only differ due to the differences in the optical detectors and the light sources used.

Object 112 (FIG. 1) and object 156 (FIG. 2) are depicted as continuous webs. However, object 112, object 156 and object 312 may be discrete objects or materials such as packages. Furthermore, as mentioned above, printed substrate 112, printed substrate 156 and printed substrate 312 may be made from, for example, paper, plastic, metal, or polymers of a laminate of different substrates (i.e., each substrate made of the same material or from different materials) and the like. It is noted that conveying apparatus 100 (FIG. 1), conveying apparatus 150 (FIG. 2) and conveying apparatus 300 may include additional rollers, rods and support surfaces with appropriate mechanical supports suitable for conveying printed substrates 112, 156 and 312 respectively.

In the embodiments shown above in FIGS. 1, 2 and 3, the non-opaque objects which are conveyed by the conveying apparatuses come in proximate contact with a backing surface, be it a plate (as in backing plate 106 (FIG. 1)), a roller (as in backing roller 156 (FIG. 2)) or a belt (as in backing belt 306 (FIG. 3)). It is noted, for example, that in the embodiments described above in FIGS. 1-3, after prolonged use in measuring chromatic characteristics, the backing, especially a white backing, may become stained and dirty, thus generating artifacts in the measured chromatic characteristics. Below, FIGS. 4, 5A, 5B and 6 show embodiments of conveying apparatuses in which non-opaque objects conveyed by the conveying apparatuses of the disclosed technique may or may not come in proximate contact with a backing surface as further described below. Nevertheless, the design of the backing surface is such that the backing surface, a backing material placed over the backing surface or the conveyed non-opaque object can be manipulated in real time so as to always present an uncontaminated measurement backing surface or material to the conveyed non-opaque object. In each of these embodiments, the backing surface is adjacent to the non-opaque object such that any chromatic characteristics measured by an optical detector represent the chromatic characteristics of the non-opaque object and any differences in the measured chromatic characteristics are merely a function of at least one of the particular optical detector used, the light source used and the relative geometry of the non-opaque object and the backing surface. In addition, as shown below, the embodiments of FIGS. 4, 5A and 5B enable a stained or dirty backing to be replaced or changed easily and quickly, thus preventing the generation of artifacts over time in the measured chromatic characteristics.

Figure 4:
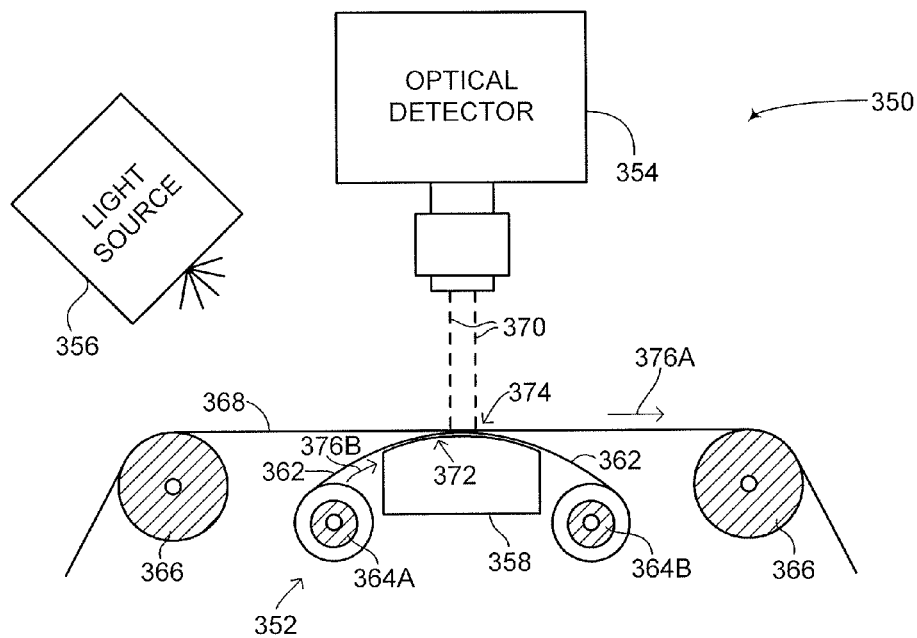
FIG. 4 is a schematic illustration of another printed material conveying apparatus, constructed and operative in accordance with another embodiment of the disclosed technique.

Reference is now made to FIG. 4 which is a schematic illustration of another printed material conveying apparatus (herein in referred to as simply a conveying apparatus), generally referenced 350, constructed and operative in accordance with another embodiment of the disclosed technique. Conveying apparatus 350 includes a backing measurement apparatus 352, an optical detector 354, a light source 356 and rollers 366. Rollers 366 and backing measurement apparatus 352 may be supported by support mechanisms (not shown). Rollers 366 convey a non-opaque object 368 in the direction of an arrow 376A. Each one of rollers 366 includes an axis (not shown) upon which it turns. In FIG. 4, object 368 is embodied as a web substrate, although object 368 can be any type of non-opaque object, as mentioned above. Object 368 can also be an opaque object as an alternative method of conveyance. Optical detector 354 is positioned above a measurement area 374 of object 368 such that a measurement of the chromatic characteristics of object 368 can be determined. This is shown schematically by dotted lines 370 in FIG. 4. Light source 356 is positioned adjacent to optical detector 354 to illuminate measurement area 374. Backing measurement apparatus 352 is positioned underneath object 368 such that a portion of backing measurement apparatus 352 comes in contact or in proximate contact with object 368 in measurement area 374, as described below. Conveying apparatus 350 may be integrated and positioned in a variety of locations within a printing system (not shown) for measuring chromatic characteristics of object 368. For example, conveying apparatus 350 may be positioned between a printing press (not shown) and a cutting machine (not shown).

Backing measurement apparatus 352 includes a set of rollers 364A and 364B, a backing material 362 and a backing support 358. Set of rollers 364A and 364B each include an axis (not shown) upon which they turn. Rollers 364A and 364B roll backing material 362 in the direction of an arrow 376B. It should be noted that backing material 362 may also be rolled in the opposite direction (not shown). As shown, arrows 376A and 376B point in the same direction. Backing support 358 includes a curved upper surface 372 and is positioned between set of rollers 364A and 364B. Backing support 358 can also be embodied as a roller. Backing support 358 is positioned directly under measurement area 374. It is noted that backing support 358 may be coupled with a plurality of motors (not shown) and additional support structures (not shown) for precisely positioning backing support 358 in relation to set of rollers 364A and 364B as well as backing material 362 and object 368. The precise position of backing support 358 determines the position, distance and tilt angles of backing material 362, in particular, in relation to object 368. Backing support 358 can be made from a rigid material or a flexible material. For example, backing support 358 can be made from a solid flexible material such as a gel, or may be a hollow solid flexible structure filled with a liquid or a gas.

Backing material 362 can be any type of flexible or solid material which can be rolled by set of rollers 364A and 364B. Backing material 362 may have different surface finishes depending on the nature of object 368 being checked and verified for chromatic characteristics. For example, backing material 362 may have an ISO standard single color finish, such as a single white color or a single black color conforming to an ISO standard, such as the ISO 13655 standard. Backing material 362 may have a standard color finish selected from a user's set of standard colors. The standard color finish may be any single color having an additional backing (not shown) or not having an additional backing. It is also noted that the outer surface of curved upper surface 372 may be coated to have a specific color finish, such as an ISO standard single color or a standard color selected from a user's set of standard colors. For example, assume object 368 is a printed web substrate which will be used to label boxes of cigarettes. The label will in turn be covered with a glossy packing material to protect it from moisture. According to the disclosed technique, the chromatic characteristics of the printed web substrate and the glossy packing material can be determined without any introduced artifacts in the measurement. The glossy packing material can be used as backing material 362, and the outer surface of curved upper surface 372 may have an ISO standard white color which conforms to the ISO 13655 standard. Therefore, the chromatic characteristics of the printed web substrate and the glossy packing material can be determined on a white backing surface. Backing material 362, the outer surface of curved upper surface 372 or both may provide additional physical properties to object 368 when its chromatic characteristics are being measured. For example, at least one of the following additional properties may be provided to object 368 at measurement area 374 via backing material 362, the outer surface of curved upper surface 372 or both: flatness, surface finish, surface texture, gloss and surface temperature. It is also noted that backing material 362 can be an actual laminating material which a user may use in a finished product. In this respect, even though backing material 362 may not conform to an ISO standard, the determination of the chromatic characteristics of object 368 with such a backing material will most closely match the color viewing conditions of the user's finished product.

In addition, according to the disclosed technique, the outer surface of curved upper surface 372 may be protected from debris, dirt, scratching or other effects which may wear it down and affect the measurement of chromatic characteristics of object 368. Accordingly, the outer surface of curved upper surface 372 may be protected via a protective coating, protective paint, a protective surface finishing (such as by being chrome plated, having a powder coated finish or via an anodization coating process) and the like. In addition, a static separation between the outer surface of curved upper surface 372 and backing material 362 may be achieved by at least one embossed section (not shown in FIG. 4) on the outer surface of curved upper surface 372, by scarifying the edges of the outer surface of curved upper surface 372 or by scarifying a particular portion of the outer surface of curved upper surface 372.

In FIG. 4, backing material 362 is rolled over backing support 358 while object 368 is rolled through conveying apparatus 350. Backing material 362 may be rolled over backing support 358 at any suitable velocity according to the nature of object 368. For example, backing material 362 may be rolled over backing support 358 at the same velocity that object 368 is conveyed over rollers 366. Thus backing material 362 remains substantially free of stains from object 368 and other debris which could alter the measured chromatic characteristics as determined by optical detector 354. In addition, since backing material 362 is rolled over backing support 358, backing material 362 is also kept clean and "pure" in terms of its color characteristics. For example, backing material 362 may be used like backing plate 106 (FIG. 1) or backing belt 306 (FIG. 3) in the sense that backing material is not rolled simultaneously as object 368 is conveyed over rollers 366. After a predetermined time or a predetermined distance object 368 has traveled over backing material 362, an inspection can be made of backing material 362 for stains or changes in its color characteristics. The inspection may be a manual inspection by a person or an automatic inspection by an inspection device. For example, an optical sensor (not shown) coupled with backing support 358 may be embodied to automatically inspect the surface of backing surface 362 for changes in its color characteristics. If the inspection determines that the color characteristics of backing material 362 have altered, or have altered beyond a predefined tolerance limit, then backing material 362 is advanced forward in the direction of arrow 376B. Once backing material 362 has been completely used, it can be easily replaced with another roll of the backing material. According to another embodiment of the disclosed technique, instead of inspecting backing material 362 periodically, backing material 362 can simply be rolled over backing support 358 at the same rate that object 368 is conveyed over rollers 366, thereby obviating the need for inspecting backing material 362 as it is assumed that backing material 362 has a uniform color over its length. Once backing material 362 is completely rolled through, another roll of backing material 362 can easily be loaded onto set of rollers 364A and 364B.

According to the disclosed technique, backing measurement apparatus 352 and in particular, the outer surface of curved upper surface 372 can be cleaned in the event that it becomes stained. Stains can be detected on the outer surface of backing measurement apparatus 352 via a manual inspection or an automatic inspection, as described above. Stains can be removed from backing measurement apparatus 352 and in particular, from the outer surface of curved upper surface 372 via a stain remover such as a chemical spray, applying heat or ultraviolet rays to the stains or by using any commonly used cleaning technique as is known to the worker skilled in the art. Backing material 362 may incorporate a cleaning agent on its underside such that backing material 362 cleans curved upper surface 372. As backing material 362 rolls over backing support 358, the cleaning agent cleans the outer surface of curved upper surface 372.

FIG. 4 shows backing measurement apparatus 352 positioned parallel to the direction of flow of object 368. Such a setup of backing measurement apparatus 352 is substantially easy to set up in a printing system, although such a setup does require ample space for the rollers of backing measurement apparatus 352. As shown below and described in greater detail in FIGS. 5A and 5B, the backing measurement apparatus in part can be positioned perpendicular to the flow of object 368. Specifically, in FIGS. 5A and 5B backing material 362 (in FIGS. 5A and 5B the backing material is numbered 408) and set of rollers 364A and 364B (in FIGS. 5A and 5B the set of rollers which roll the backing material are not shown) are positioned perpendicular to the flow of object 368. Such a setup affords significant space saving as ample space is only needed to accommodate the backing material. In addition, the backing material in such a perpendicular setup should be the width of the image of object 368 taken by optical detector 354. Since the width of the image of object 368 is usually significantly less than the width of object 368, less backing material is needed in the setup of FIGS. 5A and 5B as compared with the amount of backing material 362 used in FIG. 4, which is substantially the width of object 368.

Backing measurement apparatus 352 may additionally include a feeding mechanism (not shown), a plurality of servomechanisms (not shown) and the like, for rapidly shifting the position of backing material 362 in relation to the position of object 368 in a precise manner. Backing support 358 is used together with set of rollers 364A and 364B to define the following aspects of backing material 362: its shape, flatness and texture. These aspects can be defined based on the curvature of curved upper surface 372, the angular velocity at which set of rollers 364A and 364B rotate at as well as the tension which backing material 362 is held under. According to other embodiments of the disclosed technique, backing material 362 may be directly supported by backing support 358. Also, backing material 362 may be supported by at least one static support (not shown) on the outer surface of upper curved surface 372.

Figure 5A:
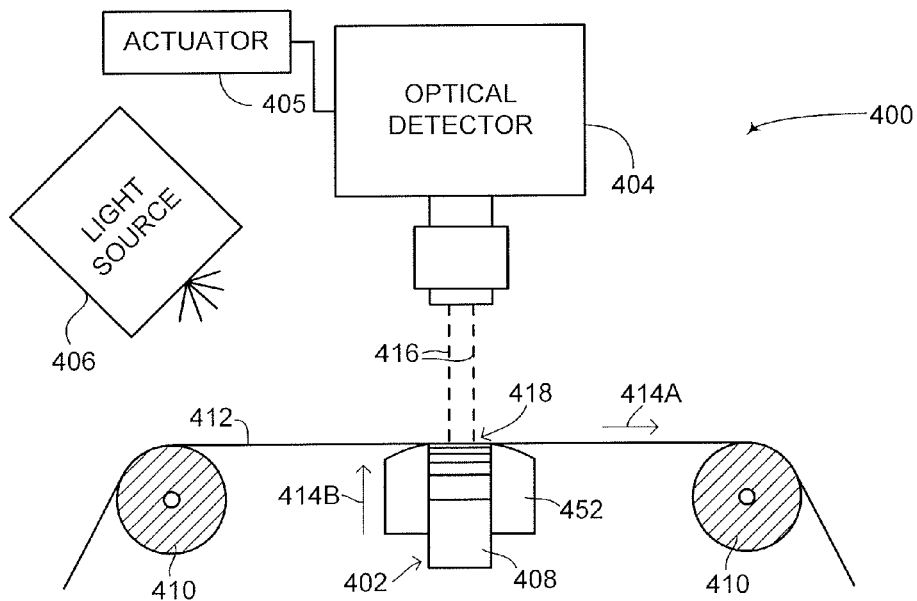
FIGS. 5A and 5B are schematic illustrations of a further printed material conveying apparatus, shown from a side view and a perspective view respectively, constructed and operative in accordance with a further embodiment of the disclosed technique.
Figure 5B:
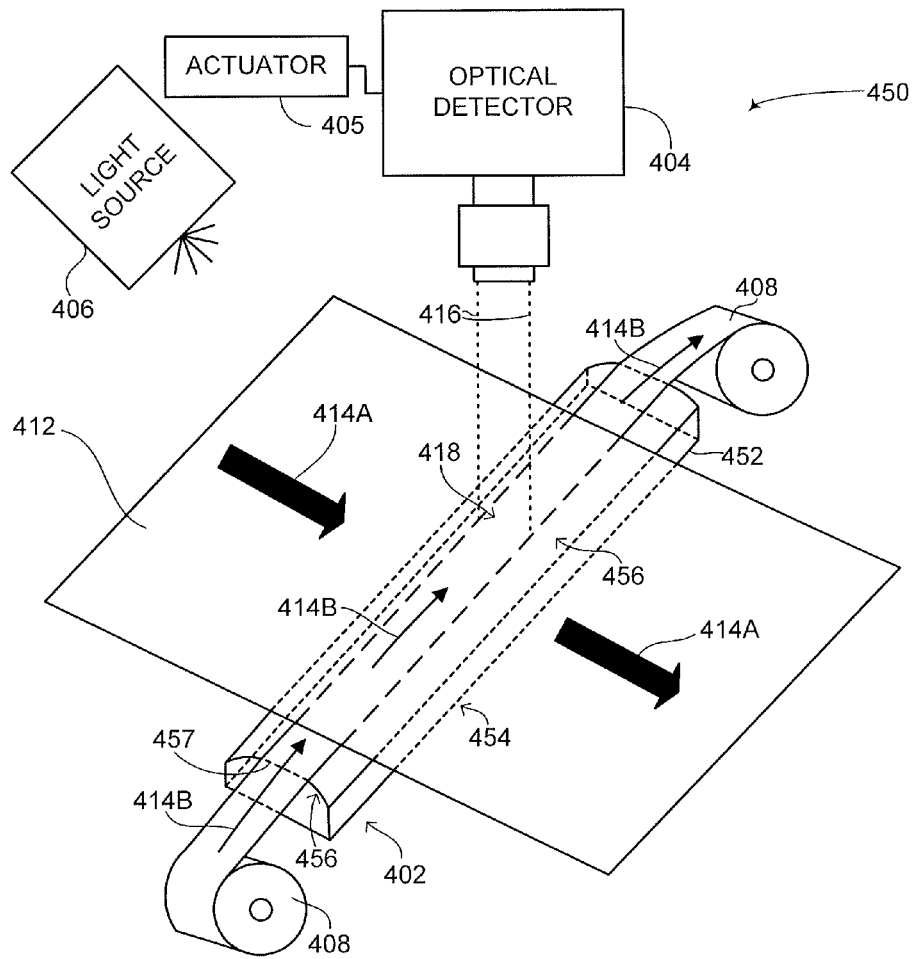

Reference is now made to FIGS. 5A and 5B which are schematic illustrations of a further printed material conveying apparatus (herein in referred to as simply a conveying apparatus), generally referenced 400 and 450 respectively, shown from a side view and a perspective view respectively, constructed and operative in accordance with a further embodiment of the disclosed technique. Elements visible in both FIGS. 5A and 5B are labeled using identical numbering. With reference to FIG. 5A, conveying apparatus 400 includes a backing measurement apparatus 402, an optical detector 404, a light source 406 and rollers 410. Rollers 410 and backing measurement apparatus 402 may be supported by support mechanisms (not shown). Rollers 410 convey a non-opaque object 412 in the direction of an arrow 414A. Each one of rollers 410 includes an axis (not shown) upon which it turns. In FIGS. 5A and 5B, object 412 is embodied as a web substrate, although object 412 can be any type of non-opaque object, as mentioned above. Object 412 can also be an opaque object, as mentioned above. Optical detector 404 is positioned above a measurement area 418 of object 412 such that a measurement of the chromatic characteristics of object 412 can be determined. This is shown schematically by dotted lines 416 in FIGS. 5A and 5B. Light source 406 is positioned adjacent to optical detector 404 to illuminate measurement area 418. Backing measurement apparatus 402 is positioned underneath object 412 in a perpendicular manner such that a portion of backing measurement apparatus 402 comes in contact or in proximate contact with object 412 in measurement area 418, as described below. Conveying apparatus 400 may be integrated and positioned in a variety of locations within a printing system (not shown) for measuring chromatic characteristics of object 412. For example, conveying apparatus 400 may be positioned between a printing press (not shown) and a cutting machine (not shown).

Backing measurement apparatus 402 includes a set of rollers (not shown), a backing material 408 and a backing support 452. The set of rollers each include an axis (not shown) upon which they turn. The set of rollers roll backing material 408 in the direction of an arrow 414B. Arrow 414B points in a direction which is into the page and is perpendicular to the direction of arrow 414A. This is shown more clearly in FIG. 5B. Backing support 452 includes a curved upper surface (not shown), a sensor (not shown) as described above, and is positioned between the set of rollers. The curvature of the curved upper surface in FIGS. 5A and 5B can be similar to the curvature of curved upper surface 372 (FIG. 4). In this respect, the curved upper surface of backing support 452 includes a central portion which is flat across object 412 and is thus in contact or in proximate contact with object 412. In addition, the curvature of the curved upper surfaces in FIGS. 5A and 5B (element 456 in FIG. 5B) may also have a compound curvature which is both parallel and perpendicular to the direction of the conveyed material or object. Conveying apparatus 400 includes other elements and components, such as motors (not shown), servomechanisms (not shown), feeding mechanisms (not shown) and the like, as described above in FIG. 4. Conveying apparatus 400 and in particular backing measurement apparatus 402 operate in a manner similar to conveying apparatus 350 (FIG. 4) except that backing measurement apparatus 402 is positioned perpendicularly to the direction in which object 412 moves.

With reference to FIG. 5B, backing measurement apparatus 402 is shown more clearly, including backing support 452 and the perpendicular nature of backing measurement apparatus 402 in relation to object 412. As shown, arrows 414A and 414B are perpendicular to one another. In addition, the width (not labeled) of backing material 408 is selected to substantially correspond to the width of measurement area 418, as shown by dotted lines 416. Backing support 452 is positioned directly under measurement area 418. Backing support 452 includes a flat bottom surface 454 and a curved upper surface 456. As shown, curved upper surface 456 has a central portion 457 which is flat across object 412. In the case that backing support 452 has a compound curvature, as described below in FIG. 6, only central portion 457 is flat. Other sections of curved upper surface 456 may have a particular curvature. Curved upper surface 456 is substantially similar to curved upper surface 372 (FIG. 4). Central portion 457 enables backing material 408 to be in contact or in proximate contact with object 412 at measurement area 418. Backing support 452 includes a sensor (not shown), as described above, similar to the sensor coupled with backing support 358 (FIG. 4). Furthermore, in the embodiment shown in FIGS. 5A and 5B, backing support 452 may optionally include a plurality of air knives (not shown), as described below in FIG. 6. The air knives may be located outside the area of backing support 452 covered by backing material 408. In addition, the air knives are not necessarily incorporated into backing support 452 and may be embodied as standalone elements (not shown) which are coupled with backing support 452. The plurality of air knives cause the conveyed material or object in conveying apparatus 450 to substantially float over backing material 408 in the case where positive airflow is provided, and to render the conveyed material or object in contact or in proximate contact with backing material 408 where negative airflow or vacuum is used. Not shown explicitly in FIG. 5B, backing material 408 is rolled over curved upper surface 456 via a plurality of rollers (not labeled). The plurality of rollers along with backing support 452 may be coupled with a plurality of supports (not shown), servomechanisms (not shown) and actuators (not shown), for supporting and precisely positioning backing support 452 and backing material 408 is relation to object 412. The plurality of rollers are positioned somewhat below backing support 452 such that backing material 408 exhibits a wrap angle as it rolls over curved upper surface 456 and in particular central portion 457. The precise position of backing support 452 determines the position, distance and tilt angles of backing material 408, in particular, in relation to object 412. Backing support 452 can be made from a rigid material or a flexible material. For example, backing support 452 can be made from a solid flexible material such as a gel, or may be a hollow solid flexible structure filled with a liquid or a gas.

As described above, backing measurement apparatus 402 is positioned such that backing material 408 moves in a direction (i.e., arrows 414B) which is perpendicular to the direction (i.e., arrows 414A) in which object 412 moves in. The setup shown in FIG. 5B, as compared to the setup shown in FIG. 4, economizes on material since a narrower strip of backing material 408 is required to back object 412. In addition, the setup of FIG. 5B economizes on space since smaller rollers can be used to roll backing material 408. However, the use of backing material 408 for backing object 412 when chromatic characteristics are measured using light source 406 and optical detector 404 may be more complex in conveying apparatus 450 since the direction of movement of backing material 408 is not parallel to the direction of movement of object 412. In general, backing material 408 may not necessarily be rolled over backing support 452 as object 412 is rolled through conveying apparatus 450. A section of backing material 408 may be used to back object 412 for a predetermined amount of time or for a predetermined length of object 412, or both. After the predetermined amount of time or length, an inspection may be done of backing material 408 and the outer surface of curved upper surface 456 for stains, dirt and debris. The inspection may be manual or automatic, utilizing the sensor (not shown) coupled with backing support 452 as described above. Depending on the results of the inspection, backing material 408 may be advanced such that an unused section of backing material 408 is substantially adjacent to measurement area 418. In addition, the outer surface of curved upper surface 456 may be cleaned of stains using methods as described above in FIG. 4. Once a roll of backing material 408 is completely used up, backing material 408 is removed from its rollers (not shown) and a new roll (not shown) of backing material 408 is loaded onto the rollers.

Figure 6:
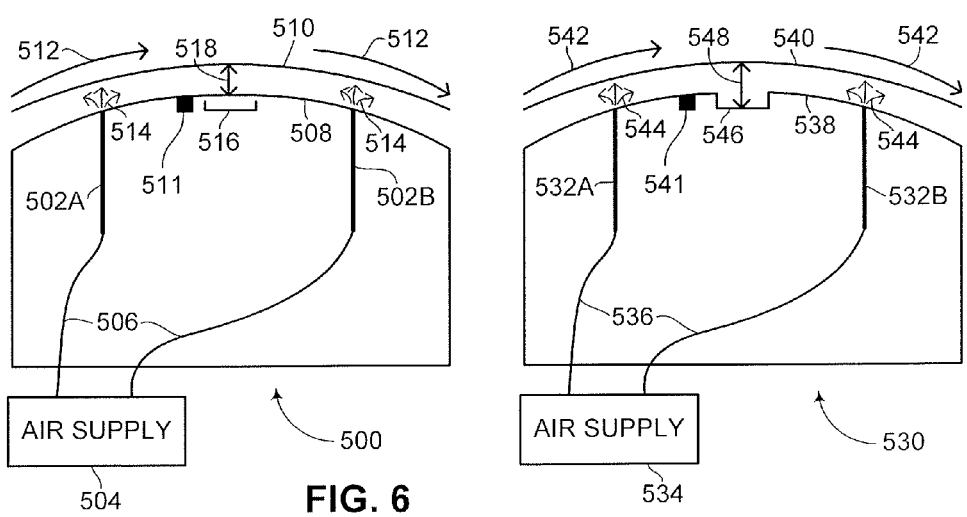
FIG. 6 is a schematic illustration of measurement backing structures for use with a printed material conveying apparatus, constructed and operative in accordance with another embodiment of the disclosed technique.

According to another aspect of the disclosed technique, there are circumstances in which it is desirable that the non-opaque objects conveyed by the conveying apparatus of the disclosed technique do not come into contact with a backing surface, yet the backing surface still enables chromatic characteristics of the non-opaque objects to be determined. Reference is now made to FIG. 6 which is a schematic illustration of measurement backing structures for use with a printed material conveying apparatus (herein in referred to as simply a conveying apparatus), generally referenced 500 and 530, constructed and operative in accordance with another embodiment of the disclosed technique. Measurement backing structure 500 includes two air knives 502A and 502B and a curved upper surface 508. It is noted that measurement backing structure 500 may include only a single air knife (not shown) or a plurality of air knives (not shown). In a preferred embodiment of the disclosed technique, measurement backing structure 500 includes two air knives 502A and 502B. Measurement backing structure 500 may be coupled with an air supply 504. Air supply 504 supplies air to the air knives, such as air knife 502A, air knife 502B or both, via a plurality of tubes 506. It is noted that the location of air knives 502A and 502B in FIG. 6 represent one possible positioning of the air knives on curved upper surface 508. Other configurations of the positioning of the air knives on or around curved upper surface 508 are possible and are a matter of design choice. Furthermore it can be appreciated by those skilled in the art that air knives need not be incorporated directly inside conveying apparatuses 500 and 530 respectively. When air is supplied to at least one of air knives 502A or 502B, air is expelled to the outer surface of curved upper surface 508. This is shown schematically by a plurality of arrows 514. The expelled air generates an additional thin film of air which separates the outer surface of curved upper surface 508 from an object 510, such as a web substrate, which travels over curved upper surface 508, as shown by a plurality of arrows 512. The thin film of air naturally follows the shape of curved upper surface 508. The thin film of air can be defined by its thickness, or in other words, the distance between the outer surface of curved upper surface 508 and object 510. This is shown schematically in FIG. 6 by a double-headed arrow 518. In general, measurement backing structure 500 is coupled with a conveying apparatus (not shown), such as a printing press, for enabling chromatic characteristics of object 510 to be determined. As shown above in FIGS. 4-5B, measurement backing structure 500 is usually coupled with an optical sensor (not shown) and a light source (not shown). It is also noted that as object 510 travels over curved upper surface 508, a thin film of air is self-generated due to the phenomenon of air entrainment. Air entrainment is exhibited when a moving surface of an object drags a thin layer of air next to the moving surface in the direction of motion of the moving surface. The phenomenon is due to the interaction of ambient air and the surface characteristics of object 510 as well as of curved upper surface 508 (such as surface roughness, flatness, porosity and the like). Furthermore, the thickness of the entrained air layer is additionally influenced by the velocity of object 510, the tension of object 510, the curvature of curved upper surface 508 and the wrap angle of object 510 over curved upper surface 508.

The thickness of the thin film of air can be monitored and controlled by a monitoring sensor 511 coupled with measurement backing structure 500. The monitoring sensor 511 may be integrated into measurement backing structure 500 (not shown), or may be mounted externally to the structure, in such a position as to be able to detect the displacement between object 510 and curved upper surface 508. The monitoring sensor 511 could be embodied, for example, as an ultrasonic sensor, an optical reflection sensor, a capacitive sensor and the like, and can be used to determine the displacement between object 510, as it is conveyed, and curved upper surface 508. The underlying curvature of curved upper surface 508 determines to some extent the amount of entrained air which inherently flows over curved upper surface 508. The amount of entrained air determines the thickness (as shown by double-headed arrow 518) of the thin film of air in the absence of any supplemental air supplied by at least one of air knives 502A or 502B. The curvature of curved upper surface 508 can be determined based on known run conditions of the conveying apparatus coupled with measurement backing structure 500. The run conditions can include the velocity and tension of object 510 as it passes over curved upper surface 508. The run conditions can include other characteristics of object 510 and curved upper surface 508. This is described in the following articles: "Characteristics of Air Film Thickness and Flow Visualization for Transporting Film" to Aoki and Hashimoto, published in the Journal of Fluid Science and Technology, volume 5, number 3, 2010, pages 503-514, and "Air Film Thickness Estimation in Web Handling Processes" to Hashimoto, published in the Transactions of the ASME—Journal of Tribology, volume 121, January 1999, pages 50-55. It is noted that the curvature of upper curved surface 508 can be modeled after known curved surfaces, such as the one described in U.S. Pat. No. 4,956,737 to Brock, assigned to the Eastman Kodak Company. In addition, changing the velocity and volume of air flow of the air expelled from air knives 502A and 502B, including the possible use of negative air flow or vacuum, can affect the thickness of the thin film of air. As shown in measurement backing structure 500, a central portion 516 of curved upper surface 508 represents the area of the outer surface of curved upper surface 508 which is aligned with an optical detector (not shown). According to one embodiment of the disclosed technique, the entire outer surface of curved upper surface 508 is coated, painted or finished with a specific color, texture or finishing and may conform to a particular ISO standard or to a user defined standard. According to another embodiment of the disclosed technique, only central portion 516, where an image is taken by the optical detector, is coated, painted or finished. In addition, according to the disclosed technique, the outer surface of curved upper surface 508 may be protected from debris, dirt, scratching or other effects which may wear down or stain the outer surface of curved upper surface 508. Accordingly, the outer surface of curved upper surface 508 may be protected via a protective coating, protective paint, a protective surface finishing (such as by being chrome plated, having a powder coat finish, or via an anodization coating process), except for central portion 516 where an image of object 510 is taken by the optical detector. According to the disclosed technique, the distance between curved upper surface 508 and object 510, as shown by double-headed arrow 518, is monitored. Any changes in the thickness of the thin film (as shown by double-headed arrow 518) may result in a change of the position of the optical detector such that the distance (not shown) between object 510 and the optical detector remains substantially constant or at least within a predefined tolerance zone. An actuator (e.g., actuator 405 in FIGS. 5A and 5B), coupled with the optical detector and with the monitoring sensor 511, may be used to rapidly change the position of the optical detector in correspondence to changes in the thickness of the thin film. According to another embodiment of the disclosed technique, the distance between the optical detector and object 510 may be kept substantially constant or at least within a predefined tolerance zone by physically moving support structure 500 towards or away from object 510. According to a further embodiment, this maintenance of the thickness of the thin film of air can be achieved by modifying the air velocity and the volume of the air expelled, or extracted from air knives 502A and 502B which affects the thickness of the thin film of air. It is also noted that a static separation (not shown) between the outer surface of curved upper surface 508 and object 510 may be achieved by at least one embossed section (not shown) on the outer surface of curved upper surface 508, by scarifying the edges of the outer surface of curved upper surface 508 or by scarifying a particular portion of the outer surface of curved upper surface 508.

Measurement backing structure 530 is similar to measurement backing structure 500 and includes two air knives 532A and 532B and a curved upper surface 508. As mentioned above, measurement backing structure 530 can include a single air knife (not shown) or a plurality of air knives (not shown). In the preferred embodiment of the disclosed technique, measurement backing structure 530 includes two air knives 532A and 532B. In addition, measurement backing structure 530 can be coupled with a conveying apparatus (not shown), such as a printing press, and is also coupled with an optical detector (not shown) as well as a light source (not shown) for determining chromatic characteristics of an object 540. Measurement backing structure 530 may be coupled with an air supply 534. Air supply 534 supplies air to air knives 532A and 532B via a plurality of tubes 536. When air is supplied to air knives 532A and 532B, air is expelled to the outer surface of curved upper surface 538. This is shown schematically by a plurality of arrows 544. The expelled air generates a thin film of air which separates the outer surface of curved upper surface 538 from an object 540, such as a web substrate, which travels over curved upper surface 538, as shown by a plurality of arrows 542. The thin film of air can be defined by its thickness, or in other words, the distance between the outer surface of curved upper surface 538 and object 540. This is shown schematically in FIG. 6 by a double-headed arrow 548. The thickness of the thin film of air can be monitored and controlled by a monitoring sensor 541 coupled with measurement backing structure 530. The monitoring sensor 541 may be integrated into measurement backing structure 530 or may be mounted externally to measurement backing structure 530 in such a position so as to be able to detect the displacement between object 540 and curved upper surface 538. The monitoring sensor 541 could be implemented, for example, as an ultrasonic sensor, an optical reflection sensor, a capacitive sensor and the like, and can be used to determine the displacement between object 540, as it is conveyed, and curved upper surface 538. As discussed previously, the underlying curvature of curved upper surface 538 determines to some extent the amount of entrained air which inherently flows over curved upper surface 538. The amount of entrained air determines the thickness (as shown by double-headed arrow 548) of the thin film of air in the absence of any supplemental air supplied by at least one of air knives 532A or 532B. The curvature of curved upper surface 538 can be determined based on known run conditions of the conveying apparatus coupled with measurement backing structure 530, including but not limited to the velocity and tension of object 540 as it passes over curved upper surface 538. The run conditions can include other characteristics of object 540 and curved upper surface 538. In addition, a change in the velocity and volume of air flow, including the possible use of negative air flow or vacuum, of the air expelled from air knives 532A and 532B, as well as modifying the velocity at which object 540 travels over curved upper surface 538 can affect the thickness (as shown by double-headed arrow 548) of the thin film of air. In measurement backing structure 530, a central portion 546 of curved upper surface 538 is impressed and engraved in curved upper surface 538. Central portion 546 is substantially similar to central portion 516 except that central portion 546 never comes into contact with object 540, even if air supply 534 is turned off (or if air is extracted) and no thin film of air is present at the outer surface of curved upper surface 538. In measurement backing structure 530, additional backing materials (not shown) can be placed in central portion 546 without worry of the additional backing materials being stained from object 540. The additional backing materials can include ceramic, plastic or paper materials and the like, as well as materials used for backing materials 362 (FIG. 4) and 408 (FIGS. 5A and 5B). In addition, according to the disclosed technique, the outer surface of curved upper surface 538 may be protected from debris, dirt, scratching or other effects which may wear down or stain the outer surface of curved upper surface 538. Accordingly, the outer surface of curved upper surface 538 may be protected via a protective coating, protective paint, a protective surface finishing (such as by being chrome plated, having a powder coat finish, or via an anodization coating process) and the like.

It is also noted that measurement backing structures 500 and 530 may have a different shape than the shape shown in FIG. 6. For example, each of measurement backing structures 500 and 530 may have circular shapes. As another example, the optical detector may be coupled with a beam (not shown). The beam may be distorted and may cause a distortion in images taken with the optical detector. Measurement backing structures 500 and 530 may be shaped to match the distortion of the beam, thereby compensating for the distortion in the beam. It is furthermore noted that either one of measurement backing structures 500 and 530 may be used as the support structure in conveying apparatus 400 (FIG. 5A) or 450 (FIG. 5B). Backing support 452 may be embodied as measurement backing structure 500 or 530. Such a backing support would have a compound curvature and a compound curved surface.

It will be appreciated by persons skilled in the art that the disclosed technique is not limited to what has been particularly shown and described hereinabove. Rather the scope of the disclosed technique is defined only by the claims, which follow.

The invention claimed is:

1. A conveying apparatus for conveying an object, said object having at least a non-opaque portion, comprising:
a light source, for illuminating said object;
an optical detector, for acquiring information at least relating to at least one chromatic characteristic of said non-opaque portion; and
a measurement backing structure, said measurement backing structure including:
a backing material exhibiting determined chromatic characteristics and determined optical characteristics; and
at least one air knife for generating a thin film of air between said object and said backing material,
wherein light emitted by said light source optically interacts with said backing material consistently through said non-opaque portion.

2. The conveying apparatus according to claim 1, wherein said object is a web substrate.

3. The conveying apparatus according to claim 1, wherein said optical detector is positioned above a measurement area of said object.

4. The conveying apparatus according to claim 3, wherein said light source is positioned adjacent to said optical detector for illuminating said measurement area.

5. The conveying apparatus according to claim 1, wherein said measurement backing structure includes a plurality of rollers for rolling said backing material over said backing structure.

6. The conveying apparatus according to claim 1, said measurement backing structure comprising a curved upper surface.

7. The conveying apparatus according to claim 6, wherein at least one of said backing material and an outer surface of said curved upper surface provide at least one physical property to said non-opaque portion.

8. The conveying apparatus according to claim 7, wherein said at least one physical property is selected from the list consisting of:
flatness;
surface finish;
surface texture;
gloss; and
surface temperature.

9. The conveying apparatus according to claim 6, said curved upper surface comprising a protection.

10. The conveying apparatus according to claim 9, wherein said protection is selected from the list consisting of:
a protective coating;
protective paint;
a protective surface finishing;
a chrome plated finish;
a powder coated finish;
an anodization coating process; and
a static separation between an outer surface of said curved upper surface and said backing material via at least one embossed section on said outer surface of said curved upper surface.

11. The conveying apparatus according to claim 1, said measurement backing structure comprising a stain remover for removing at least one stain from said backing material.

12. The conveying apparatus according to claim 11, wherein said stain remover is selected from the list consisting of:
a chemical spray;
applying heat to said at least one stain;
applying ultraviolet rays to said at least one stain; and
incorporating a cleaning agent on an underside of said backing material.

13. The conveying apparatus according to claim 1, wherein said measurement backing structure is positioned substantially perpendicular to a direction in which said object is conveyed.

14. The conveying apparatus according to claim 13, wherein a width of said backing material is substantially similar to a width of a measurement area of said object.

15. The conveying apparatus according to claim 1, wherein said at least one air knife is incorporated into an upper surface of said measurement backing structure.

16. The conveying apparatus according to claim 1, wherein said at least one air knife is coupled with said measurement backing structure.

17. The conveying apparatus according to claim 1, wherein said at least one air knife causes said object to float over said backing material.

18. The conveying apparatus according to claim 1, said measurement backing structure further comprising:
an air supply, for supplying air to said at least one air knife; and at least one respective tube, coupled with said at least one air knife and said air supply.

19. The conveying apparatus according to claim 1, wherein a thickness of said thin film of air is determined according to at least one factor.

20. The conveying apparatus according to claim 19, wherein said at least one factor is selected from the list consisting of:
- a velocity of air flow expelled from said at least one air knife;
- a volume of air flow expelled from said at least one air knife;
- a velocity of air flow extracted from said at least one air knife;
- a volume of air flow extracted from said at least one air knife;
- run conditions of said conveying apparatus;
- a velocity of said object over said measurement backing structure; and
- a tension of said object over said measurement backing structure.

21. The conveying apparatus according to claim 1, wherein said measurement backing structure has a circular shape.

22. The conveying apparatus according to claim 1, further comprising a beam, coupled with said optical detector,
wherein said beam is distorted; and
wherein said measurement backing structure is shaped to match said distortion of said beam.

23. A conveying apparatus for conveying an object, said object having at least a non-opaque portion, comprising:
- a light source, for illuminating said object;
- an optical detector, for acquiring information at least relating to at least one chromatic characteristic of said non-opaque portion; and
- a measurement backing structure, said measurement backing structure including:
  - a backing material exhibiting determined chromatic characteristics and determined optical characteristics,
  - wherein a thin film of air exists between said object and said backing material, and
  - wherein light emitted by said light source optically interacts with said backing material consistently through said non-opaque portion.

24. The conveying apparatus according to claim 10, wherein said curved upper surface includes a central portion, wherein said central portion is flat and said backing material is positioned over said central portion.

25. The conveying apparatus according to claim 24, wherein said central portion comprises a protection, wherein said protection is selected from the list consisting of:
- a coating;
- a painting; and
- a finishing.

26. The conveying apparatus according to claim 24, wherein said backing material is positioned in said central portion of said measurement backing structure, such that said object is not in contact with said backing material when said object is conveyed.

27. The conveying apparatus according to claim 26, wherein at least one additional backing material is placed in said central portion.

28. The conveying apparatus according to claim 27, wherein said at least one additional backing material is selected from the list consisting of:
- ceramic materials;
- plastic materials;
- paper materials; and
- materials used for said backing material.

29. The conveying apparatus according to claim 5, wherein said plurality of rollers roll said backing material at a substantially similar velocity to a velocity at which said object is conveyed.

30. The conveying apparatus according to claim 5, wherein said backing material is advanced if a portion of said backing material in said measurement area is determined to have at least one altered color characteristic beyond a predefined tolerance limit.

31. The conveying apparatus according to claim 19, wherein a distance between said object and said optical detector is kept constant by modifying said thickness according to said at least one factor.

32. The conveying apparatus according to claim 19, said measurement backing structure further comprising a monitoring sensor for detecting said thickness of said thin film of air.

33. The conveying apparatus according to claim 32, wherein said monitoring sensor is selected from the list consisting of:
- an ultrasonic sensor;
- an optical reflection sensor; and
- a capacitive sensor.

34. The conveying apparatus according to claim 32, further comprising an actuator, coupled with said optical detector and said monitoring sensor, for changing a position of said optical detector in correspondence to a change in said thickness of said thin film of air.

35. The conveying apparatus according to claim 32, wherein a distance between said object and said optical detector is kept constant by moving said measurement backing structure.

36. The conveying apparatus according to claim 2, wherein said web substrate is made of a material selected from the group consisting of:
- paper;
- plastic;
- flexible polymer; and
- metal.

37. The conveying apparatus according to claim 36, wherein said web substrate is composed of a laminate of at least two materials.

* * * * *